United States Patent
Wang et al.

(10) Patent No.: US 9,637,423 B1
(45) Date of Patent: May 2, 2017

(54) INTEGRATED PROCESS FOR MAKING HIGH-OCTANE GASOLINE

(71) Applicant: ExxonMobil Research and Engineering Company, Annandale, NJ (US)

(72) Inventors: Kun Wang, Bridgewater, NJ (US); Shamel Merchant, Bridgewater, NJ (US)

(73) Assignee: EXXONMOBIL RESEARCH AND ENGINEERING COMPANY, Annandale, NJ (US)

( * ) Notice: Subject to any disclaimer, the term of this patent is extended or adjusted under 35 U.S.C. 154(b) by 0 days.

(21) Appl. No.: 15/388,013

(22) Filed: Dec. 22, 2016

Related U.S. Application Data

(63) Continuation-in-part of application No. 14/956,477, filed on Dec. 2, 2015.

(60) Provisional application No. 62/092,485, filed on Dec. 16, 2014.

(51) Int. Cl.
```
C07C 2/76      (2006.01)
C07C 2/82      (2006.01)
C07C 29/00     (2006.01)
C10G 53/14     (2006.01)
C07C 1/24      (2006.01)
C07C 2/06      (2006.01)
C07C 2/86      (2006.01)
C10L 1/06      (2006.01)
C10L 1/08      (2006.01)
C10L 10/10     (2006.01)
C10L 10/12     (2006.01)
C07C 409/04    (2006.01)
C07C 409/16    (2006.01)
C07C 29/48     (2006.01)
```

(52) U.S. Cl.
CPC .............. *C07C 2/862* (2013.01); *C07C 29/48* (2013.01); *C07C 409/04* (2013.01); *C07C 409/16* (2013.01); *C10L 1/06* (2013.01); *C10L 1/08* (2013.01); *C10L 10/10* (2013.01); *C10L 10/12* (2013.01); *C10L 2200/0423* (2013.01); *C10L 2200/0446* (2013.01); *C10L 2270/023* (2013.01); *C10L 2270/026* (2013.01)

(58) Field of Classification Search
CPC .. C07C 2/76; C07C 2/82; C07C 29/00; C10G 53/14
USPC .................. 585/700, 709, 639, 510; 208/49; 568/909.8
See application file for complete search history.

(56) References Cited

U.S. PATENT DOCUMENTS

| | | | |
|---|---|---|---|
| 2,845,461 | A | 7/1958 | Winkler et al. |
| 3,478,108 | A | 11/1969 | Grace |
| 3,594,320 | A | 7/1971 | Orkin |
| 3,775,325 | A | 11/1973 | Kerfoot et al. |
| 3,862,024 | A | 1/1975 | Favis |
| 4,140,619 | A | 2/1979 | van der Wiel et al. |
| 4,175,278 | A | 11/1979 | Sato et al. |
| 4,408,081 | A | 10/1983 | Foster |
| 4,594,172 | A | 6/1986 | Sie |
| 4,618,737 | A | 10/1986 | Chester et al. |
| 4,883,581 | A | 11/1989 | Dickakian |
| 4,911,821 | A | 3/1990 | Katzer et al. |
| 4,913,794 | A | 4/1990 | Le et al. |
| 4,919,788 | A | 4/1990 | Chen et al. |
| 4,975,177 | A | 12/1990 | Garwood et al. |
| 4,990,713 | A * | 2/1991 | Le .......................... C10G 50/02 585/332 |
| 4,997,543 | A | 3/1991 | Harandi et al. |
| 5,008,460 | A | 4/1991 | Garwood et al. |
| 5,021,142 | A | 6/1991 | Bortz et al. |
| 5,037,528 | A | 8/1991 | Garwood et al. |
| 5,149,885 | A | 9/1992 | Jubin, Jr. |
| 5,162,593 | A | 11/1992 | Maffia et al. |
| 5,171,916 | A | 12/1992 | Le et al. |
| 5,243,084 | A | 9/1993 | Cochran et al. |
| 5,271,825 | A | 12/1993 | Bortz et al. |
| 5,288,919 | A | 2/1994 | Faraj |
| 5,306,416 | A | 4/1994 | Le et al. |
| 5,345,009 | A | 9/1994 | Sanderson et al. |

(Continued)

FOREIGN PATENT DOCUMENTS

| | | |
|---|---|---|
| CA | 1103913 A | 6/1981 |
| CA | 2098995 A1 | 7/1992 |

(Continued)

OTHER PUBLICATIONS

PCT/US2015/063394 International Search Report and Written Opinion dated Mar. 18, 2016.

(Continued)

*Primary Examiner* — Thuan D Dang
(74) *Attorney, Agent, or Firm* — Andrew T. Ward

(57) ABSTRACT

An integrated process for converting low-value paraffinic materials to high octane gasoline and high-cetane diesel light is disclosed. The process involves: (1) oxidation of an iso-paraffin to alkyl hydroperoxide and alcohol; (2) converting the alkyl hydroperoxide and alcohol to dialkyl peroxide; (3) converting low-octane, paraffinic gasoline molecules using the dialkyl peroxides as radical initiators, thereby forming high-cetane diesel, while the dialkyl peroxide is converted to an alcohol; (4) converting the alcohol to an olefin; and (5) alkylating the olefin with iso-butane to form high-octane alkylate. The net reaction is thus conversion of iso-paraffin to high-octane gasoline alkylate, and conversion of low-octane paraffinic gasoline to high-cetane diesel.

14 Claims, No Drawings

(56) References Cited

U.S. PATENT DOCUMENTS

| | | | |
|---|---|---|---|
| 5,705,724 | A | 1/1998 | Collins et al. |
| 5,750,480 | A | 5/1998 | Xiong et al. |
| 7,034,189 | B1 | 4/2006 | Kollar |
| 7,723,556 | B2 | 5/2010 | Elomari et al. |
| 7,732,654 | B2 | 6/2010 | Elomari et al. |
| 7,973,204 | B2 | 7/2011 | Elomari et al. |
| 2008/0253936 | A1 | 10/2008 | Abhari |
| 2016/0168048 | A1 | 6/2016 | Wang et al. |

FOREIGN PATENT DOCUMENTS

| | | |
|---|---|---|
| DE | 2453863 A1 | 5/1975 |
| DE | 298521 A5 | 2/1992 |
| EP | 0104729 A2 | 4/1984 |
| FR | 2210656 A1 | 7/1974 |
| FR | 2210657 A1 | 7/1974 |
| JP | 49034903 A | 3/1974 |
| JP | 51012802 A | 1/1976 |
| JP | 60108495 A | 6/1985 |
| NL | 7510598 A | 3/1977 |
| PL | 63556 Y1 | 12/1969 |
| SU | 1068467 A1 | 1/1984 |
| SU | 438293 A1 | 11/1984 |
| SU | 1525196 A1 | 11/1989 |
| SU | 1778148 A1 | 11/1992 |
| SU | 1799902 A1 | 3/1993 |
| SU | 1810378 A1 | 4/1993 |

OTHER PUBLICATIONS

Wallner et al., "Analytical Assessment of C2-C8 Alcohols as Spark-Ignition Engine Fuels", Proceedings of the FISITA 2012 World Automotive Congress, Nov. 7, 2012, pp. 15-26, vol. 3, Springer.

Unknown, "Advanced Motor Fuels", Implementing Agreement for Advanced Motor Fuels, http://www.iea-amf.org/content/fuel_information/butanol/properties.

Ghosh et al., "Development of a Detailed Gasoline Composition-Based Octane Model", Industrial & Engineering Chemistry Research, Nov. 24, 2005, pp. 337-345, vol. 45, iss. 1, ACS Publications.

Perdih et al., "Topological Indices Derived from Parts of a Universal Matrix", Acta Chimica Slovenica, Apr. 28, 2006, pp. 180-190, vol. 53, Slovenian Chemical Society.

Sust, "Studies on the synthesis of lubricating oils using olefins from technical C5-fractions", Energy Res., 1983, vol. 8, iss.1, abstract only.

Grudzien, "Selective solvent separation of shale oil fractions to obtain raw material for polymerization", Koks, Smola, Gaz, 1971, pp. 336-339, vol. 16, iss. 12, abstract only.

Ouyang et al., "Production technique of synthetic hydrocarbon lube oil with coking top cycle oil", Runhuayou, 2001, pp. 17-20, vol. 15, iss. 5, abstract only.

Kuliev et al., "Production of lubricating oils by alkylation of an aromatic raw material", Sbornik Trudov—Akademiya Nauk Azerbaidzhanskoi SSR, Institut Neftekhimicheskikh Protsessov im. Yu. G. Mamedalieva, 1973, pp. 128-128, vol. 5, abstract only.

Kuliev et al., "Manufacture of synthetic lubricating oils by alkylation of a secondary oil refining product", Chemische Technik, 1971, vol. 23, iss. 1, abstract only.

Takahashi et al., "Designed Oil Products from Cracked Bottom Oil", Bull Jap Petrol Inst, May 1971, pp. 103-108, vol. 13, iss. 1, abstract only.

Mursalova et al., "Alkylation of Benzene with a Wide Fraction of Alpha-Olefins (30 Degrees-250 Degrees C) Obtained by Cracking N-Paraffins (Separated in the Urea Dewaxing) of a Transformer Oil", Dokl Akad Nauk Azerb SSR, 1969, pp. 20-23, vol. 25, iss. 7, abstract only.

Kuliev, "Alkyl derivatives of petroleum hydrocarbons as lubricating oil basestocks", Khimiya i Tekhnologiya Topliv i Masel, 1997, pp. 34-35, vol. 6, abstract only.

Graves, "STRATCO Effluent Refrigerated H2SO4 Alkylation Process", Chapter 1.2 in Handbook of Petroleum Refining Processes, 3rd Ed., 2004. McGraw-Hill.

Roeseler, "UOP Alkylene Process for Motor Fuel", Chapter 1.3 in Handbook of Petroleum Refining Processes, 3rd Ed., 2004. McGraw-Hill.

Detrick et al., "UOP HF Alkylation Technology", Chapter 1.2 in Handbook of Petroleum Refining Processes, 3rd Ed., 2004. McGraw-Hill.

\* cited by examiner

INTEGRATED PROCESS FOR MAKING HIGH-OCTANE GASOLINE

CROSS-REFERENCE TO RELATED APPLICATIONS

This application is a continuation-in-part of U.S. Ser. No. 14/956,477, filed Dec. 2, 2015, now allowed, which claims the benefit of provisional U.S. Serial Nos. 62/092,485, filed on Dec. 16, 2014, each of which is incorporated by reference herein in its entirety.

BACKGROUND

The present invention relates to an integrated process to upgrade relatively low-value paraffinic materials to high-octane gasoline and high-cetane diesel. The process is particularly applicable to the upgrading of low-value paraffinic feeds, such as iso-butane and heavy virgin naphtha to make high-octane alkylate and high-cetane diesel via oxidation.

Alkylate is composed of a mixture of high-octane, branched-chain paraffinic hydrocarbons (mostly iso-heptane and iso-octane). Alkylate is a premium gasoline blending stock because it has exceptional antiknock properties, relatively low Reid Vapor Pressure (RVP), and is clean burning. The octane number of an alkylate depends mainly upon the kind of feeds used and upon operating conditions. For example, iso-octane results from combining C4 olefins with iso-butane and has an octane rating of 100 by definition. There are other products in the alkylate, so the octane rating will vary accordingly. Current technologies for producing high octane alkylate require C4 olefins, particularly iso-butylene, which are alkylated with iso-butane using an acid catalyst, such as $H_2SO_4$, HF, or solid acids as zeolites. When C4 olefins are constrained, expensive on-purpose C4 olefin generation is utilized to provide feedstock, and requires high temperatures, low pressures, and frequent catalyst regeneration. There remains a need to develop a new process for utilizing abundant paraffins, specifically iso-butane, to produce high-octane alkylate without expensive C4 olefin as a feedstock.

High-cetane diesel (diesel with a cetane number in the range of about 40-110, preferably about 45-90, and more preferably about 50-80) is typically obtained from crude distillation, or from Fischer-Tropsch synthesis. These diesel molecules, particularly those from Fischer-Tropsch synthesis, require an additional hydro-isomerization (i.e. dewaxing) step to meet the cloud point specification for diesel. Low octane naphtha, such as heavy virgin naphtha, is typically converted to aromatics, a high octane gasoline blend, using catalytic reforming. There remains a need to utilize abundant naphthas, such as heavy virgin naphtha, heavy cat naphtha, and coker naphtha, to produce high-cetane diesel, a more carbon-efficient disposition for heavy virgin naphtha than gasoline.

Demand for high-octane gasoline and high-cetane diesel is expected to grow. Additionally, the increased supply of light paraffins in North America and the abundance of heavy virgin naptha creates a need and opportunities for upgrading to high-octane gasoline and high-cetane diesel. Disclosed herein is an integrated process for achieving both.

SUMMARY

We have now found a novel integrated process for upgrading low-value paraffinic materials to high octane gasoline and high-cetane diesel. In a first embodiment of the present invention, the process involves: (1) oxidation of an iso-paraffin to alkyl hydroperoxide and alcohol; (2) converting the alkyl hydroperoxide and alcohol to dialkyl peroxide; (3) converting low-octane, paraffinic gasoline molecules using the dialkyl peroxides as radical initiators, thereby forming high-cetane diesel, while the dialkyl peroxide is converted to an alcohol; (4) converting the alcohol to an olefin; and (5) alkylating the olefin with iso-butane to form high-octane alkylate. An alternative embodiment to Step 5 is dimerization of the olefin giving another type of high octane fuel. The net reaction is thus conversion of iso-paraffin to high-octane gasoline alkylate, and conversion of low-octane paraffinic gasoline to high-cetane diesel.

In another embodiment of the present invention, the process involves (1) oxidation of iso-butane to t-butyl hydroperoxide and t-butyl alcohol; (2) converting the t-butyl hydroperoxide and the t-butyl alcohol to di-t-butyl peroxide; (3) converting heavy naphtha, such as heavy virgin naphtha, heavy cat naphtha, or coker naphtha, using the di-t-butyl peroxide as radical initiators, thereby forming high-cetane diesel, while the di-t-butyl peroxide is converted to t-butyl alcohol; (4) converting the t-butyl alcohol to iso-butylene; and (5) alkylating the iso-butylene with iso-butane to form high-octane alkylate. An alternative to Step 5 is dimerization of the olefin giving another type of high octane fuel. The net reaction is thus conversion of iso-butane to high-octane gasoline alkylate, and conversion of heavy virgin naphtha to high-cetane diesel.

DETAILED DESCRIPTION

The present invention relates to an integrated process for upgrading low-value paraffinic materials to high octane gasoline and high-cetane diesel. The process of the present invention involves three primary steps: (1) oxidation of an iso-paraffin to alkyl hydroperoxide and alcohol; (2) converting the alkyl hydroperoxide and alcohol to dialkyl peroxide; (3) converting low-octane, paraffinic gasoline molecules using the dialkyl peroxides as radical initiators, thereby forming high-cetane diesel, while the dialkyl peroxide is converted to an alcohol; (4) converting the alcohol to an olefin; and (5) alkylating the olefin with iso-butane to form high-octane alkylate. The net reaction is thus conversion of iso-paraffin to high-octane gasoline alkylate, and conversion of low-octane paraffinic gasoline to high-cetane diesel.

In a preferred embodiment of the present invention, the iso-paraffin feedstock is iso-butane. The process proceeds as described generally above: (1) oxidation of iso-butane to t-butyl hydroperoxide and t-butyl alcohol; (2) converting the t-butyl hydroperoxide and the t-butyl alcohol to di-t-butyl peroxide; (3) converting heavy naphtha, such as heavy virgin naphtha, heavy cat naphtha, or coker naphtha, using the di-t-butyl peroxide as radical initiators, thereby forming high-cetane diesel, while the di-t-butyl peroxide is converted to t-butyl alcohol; (4) converting the t-butyl alcohol to iso-butylene; and (5) alkylating the iso-butylene with iso-butane to form high-octane alkylate. An alternative to Step 5 is dimerization of the olefin giving another type of high octane fuel. The net reaction is thus conversion of iso-butane to high-octane gasoline alkylate, and conversion of heavy virgin naphtha to high-cetane diesel.

The chemistry of Steps 1-5 with respect to iso-butane feed is shown below in corresponding Equations 1-5:

Equation 1

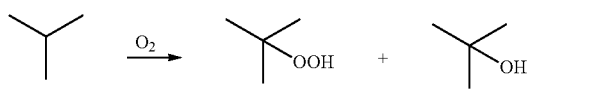

Equation 2

Equation 3

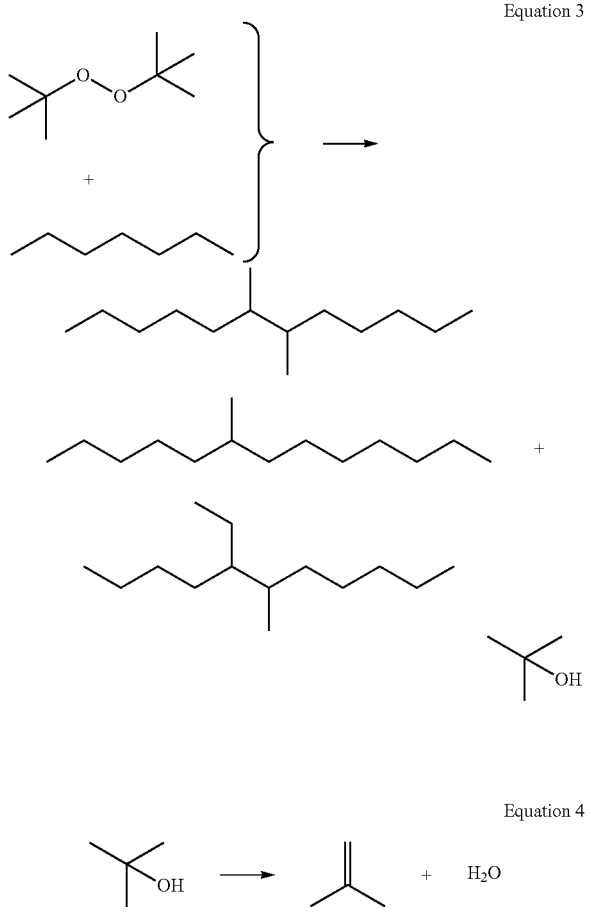

Equation 4

Steps 1 and 2 have been previously described with respect to mixed paraffinic feedstocks in applicant's co-pending application, U.S. Publ. App. No. 2016/0168048, incorporated by reference herein in its entirety. U.S. Publ. App. No. 2016/0168048 describes a process to convert light paraffins to heavier hydrocarbons generally, for example, distillates and lubricant base stocks, using coupling chemistry analogous to Steps 1 and 2 described above. Whereas U.S. Publ. App. No. 2016/0168048 is directed to mixed paraffinic feed to create distillates and lubricant base stocks, the present invention utilizes analogous coupling chemistry to create high-cetane diesel utilizing iso-paraffins such as iso-butane and iso-paraffinic gasoline as feedstock.

Iso-butane oxidation in Step 1/Equation 1 is well-established commercially for making t-butyl hydroperoxide (TBHP) for propylene oxide manufacture, with variants of the process also described, for example, in U.S. Pat. No. 2,845,461; U.S. Pat. No. 3,478,108; U.S. Pat. No. 4,408,081 and U.S. Pat. No. 5,149,885. EP 0567336 and U.S. Pat. No. 5,162,593 disclose co-production of TBHP and t-butyl alcohol (TBA). As TBA is another reactant used in Step 2 of the present invention, the present inventive process scheme utilizes Step 1 as a practical source of these two reactants. Air (~21% oxygen), a mixture of nitrogen and oxygen containing 2-20 vol % oxygen, or pure oxygen, can be used for the oxidation, as long as the oxygen-to-hydrocarbon vapor ratio is kept outside the explosive regime. Preferably air is used as the source of oxygen. Typical oxidation conditions for Step 1 of the present invention are: 110-150° C. (preferably 130 to 140° C., at a pressure of about 300-800 psig (preferably about 450-550 psig), with a residence time of 2-24 hours (preferably 6-8 h), to give a targeted conversion of 15%-70% (preferably 30-50%). Selectivity to TBHP of 50-80% and to TBA of 20-50% is typical.

In Step 2/Equation 2, the conversion of the TBHP and TBA to di-t-butyl peroxide (DTBP) is performed using an acid catalyst. For example, U.S. Pat. No. 5,288,919 describes the use of an inorganic heteropoly and/or isopoly acid catalyst (such as for the reaction of TBA with TBHP. The conjoint production of DTBP and TBA from TBHP is also described in U.S. Pat. No. 5,345,009. A preferred configuration for the present invention uses reactive distillation where product water is continuously removed as overhead by-product. Typical reaction temperature is in the range of 50-200° C., preferably 60-150° C., more preferably 80-120° C. The TBHP to TBA mole ratio is in the range of 0.5-2, preferably 0.8-1.5, more preferably 0.9-1.1. The reaction can be performed with or without a solvent. Suitable solvents comprise hydrocarbons having a carbon number greater than 3, such as paraffins, naphthenes, or aromatics. Conveniently, the unreated iso-butane from Step 1 can be used as solvent for Step 2. Pressure for the reaction is held at appropriate ranges to ensure the reaction occurs substantially in the liquid phase, for example, 0-300 psig, preferably 5-100 psig, more preferably 15-50 psig. An acid catalyst such as Amberlyst™ resin, Nafion™ resin, aluminosilicates, acidic clay, zeolites (natural or synthetic), silicoaluminophosphates (SAPO), heteropolyacids, acidic oxides such as tungsten oxide on zirconia, molybdenum oxide on zirconia, sulfunated zirconia, liquid acids such sulfuric acid, or acidic ionic liquids may be used in Step 2/Equation 2 to promote the conversion of TBHP and TBA into DTBP.

In Step 3/Equation 3, DTBP is introduced to a coupling reactor to initiate free radical coupling of heavy virgin naphtha (HVN). Typical reaction conditions for Step 3 of the present invention are: 100-170° C. (preferably about 145-155° C.), with pressure maintained to ensure that paraffins stay in the liquid or supercritical phase, typically 300-1500 psig (preferably about 500-1200 psig). Residence time is normally in the range of 2-24 hours (preferably 4-16 hours). The molar ratio of DTBP to HVN to be coupled is in the range of about 0.01-100, preferably in the range of about 0.05-10, and more preferably in the range of 0.1-2. By controlling the reaction severity for radical coupling (Equation 3), higher molecular weight products can also be obtained. Complete conversion of DTBP is normally achieved in this step. Following Step 3, the mixed product stream is fractionated, with unreacted HVN being recycled to the coupling reactor, TBA being sent to Step 4, and byproduct acetone being removed. Due to the nature of the coupling chemistry, the diesel fraction (C14-C28) are branched with short chain alkyl groups such as methyl and ethyl, yielding a resulting product having a high cetane value. It is envisioned that other heavy naphtha feeds, such as heavy cat naphtha (i.e. the heavy naphtha fraction from a catalytic cracker) or coker naphtha, are acceptable feedstock for Step 3 of this invention.

In Step 4/Equation 4, TBA is sent to a dehydration reactor, where it is dehydrated over an acid catalyst to yield iso-butylene and water. An acid catalyst such as Amberlyst™ resin, Nafion™ resin, aluminosilicates, acidic clay, alumina, zeolites (natural or synthetic), silicoaluminophosphates (SAPO), heteropolyacids, acidic oxides such as tungsten oxide on zirconia, molybdenum oxide on zirconia, sulfunated zirconia, liquid acids such sulfuric acid, or acidic ionic liquids may be used. Typical reaction temperature is in the range of 150-400° C., preferably 200-350° C., more preferably 250-350° C. Typical pressure for the reaction is 50-500 psig, preferably 100-400 psig, more preferably 200-300 psig. The reaction can be performed in fixed-bed or batch reactor. A preferred embodiment of this step utilizes reactive distillation to continuously remove co-product water.

In Step 5/Equation 5, iso-butylene (from Step 4) is sent to an alkylation reactor, where it is alkylated with iso-butane to yield high-octane alkylate. The alkylation reaction can be conducted in a wide range of reactor configurations including fixed bed (single or in series), slurry reactors, and/or catalytic distillation towers. In addition, the alkylation reaction can be conducted in a single reaction zone or in a plurality of reaction zones, preferably in a plurality of reaction zones. The mole ratio of iso-butane to iso-butylene may be in the range of 1-100, preferably 5-80, more preferably 10-50. The alkylation is conducted in the presence of an acid catalyst. Any catalyst suitable for isoparaffin alkylation, whether homogeneous or heterogeneous, may be used. Examples of suitable acidic homogeneous catalysts include hydrofluoric acid, sulfuric acid, and mixtures thereof. Examples of suitable acidic heterogeneous catalysts include chlorided alumina, fluorided alumina, zeolites, acidic metal oxides and mixed metal oxides, and mixtures thereof. Non-limiting examples of such zeolites include those of the MOR, BEA, FAU, MTW, and MWW families, preferably the FAU, MWW, and MOR families. Non-limiting examples of acidic metal oxides or mixed metal oxides include tungsten oxides (WOx), molybdenum oxide (MoOx), mixed oxides such as WOx/ZrO$_2$, WOx/CeO2, MoOx/ZrO$_2$, MoOx/CeO2, and sulfated zirconia. When a homogenous acid catalyst is used, such as hydrofluoric acid or sulfuric acid, suitable reaction temperatures range from about 0° C. and about 50° C., such as from about 5° C. and about 40° C., or from about 10° C. and about 25° C. When a heterogeneous acid catalyst is used, such as a zeolite, suitable reaction temperatures range from about 100° C. to about 400° C., preferably from about 125° C. to about 300° C., more preferably from about 150° C. to about 250° C. Irrespective of the catalyst employed, the reaction pressure is preferably maintained so that the C4 olefinic feed remains in liquid form within the reactor. For instance, suitable reaction pressures are from about 100 kPa to about 7000 kPa absolute (e.g., atmospheric to about 1000 psia), such as from about 500 kPa to about 5000 kPa absolute.

EXAMPLE

In order to provide a better understanding of the foregoing disclosure, the following non-limiting example is offered. Although the example may be directed to specific embodiments, they are not to be viewed as limiting the invention in any specific respect.

This example illustrates the general procedure for coupling n-heptane (to demonstrate HVN) using DTBP to form high-cetane diesel. In a 300 cc autoclave the following were loaded: 60 g of n-heptane and 30 g of DTBP (trade name Luperox DI from Aldrich Chemicals, 98%). The autoclave was sealed, connected to a gas manifold, and pressurized with 600 psig nitrogen. The reactor content heated under stirring (500 rpm) at a rate of 2° C./min to 150° C. and held for 4 hours. The heat was turned off and the autoclave allowed to cool down to room temperature. A sample was taken and analyzed by GC analysis, showing complete conversion of DTBP and 30% conversion of n-heptane. The autoclave was opened and the reactor content collected at the end of the run, recovering 88% of the materials loaded. The products are shown in Table 1 below:

TABLE 1

| | |
|---|---|
| Reaction temperature (° C.) | 150 |
| Time (h) | 4 |
| n-heptane loading, g | 60 |
| DTBP loading, g | 30 |
| HC wt. sel. (%) | |
| C14 | 38 |
| C14+ | 60 |
| Oxygenates wt. sel. (%) | |
| Acetone | 13 |
| t-Butanol | 87 |

As demonstrated in Table 1, a high-cetane diesel composition can be produced according to certain teachings of the present invention. Due to the nature of the coupling chemistry, the diesel fraction (C14-C28) are branched with short chain alkyl groups such as methyl and ethyl, yielding a resulting product having a high cetane value. One of ordinary skill in the art will appreciate that by controlling the reaction severity for radical coupling (Equation 3), higher molecular weight products can also be obtained. The TBA co-product can be further upgraded to high-octane alkylate using known dehydration and alkylation technologies, as described in Steps 4-5 above.

ADDITIONAL EMBODIMENTS

Embodiment 1

A process for upgrading substantially paraffinic feed to high-cetane diesel, comprising oxidizing a first feed stream comprising one or more iso-paraffins to form alkyl hydroperoxides and first alcohols, catalytically converting the alkyl hydroperoxides and first alcohols to dialkyl peroxides, and coupling a second feed stream substantially comprising paraffins using the dialkyl peroxides as a radical initiator to create high-cetane diesel and second alcohols.

Embodiment 2

A process according to embodiment 1, further comprising converting the second alcohols to olefins.

Embodiment 3

A process according to embodiment 2, further comprising alkylating the olefins with iso-paraffins to form high-octane gasoline.

Embodiment 4

A process according to embodiment 2, further comprising dimerizing the olefins to form high octane gasoline.

Embodiment 5

An integrated process for upgrading low-value paraffinic materials to high octane gasoline and high-cetane diesel, comprising oxidizing a first feed stream comprising one or more iso-paraffins to form alkyl hydroperoxides and first alcohols, catalytically converting the alkyl hydroperoxides and first alcohols to dialkyl peroxides, coupling a second feed stream substantially comprising paraffins using the dialkyl peroxides as a radical initiator to create high-cetane diesel and second alcohols, converting the second alcohols to olefins, and alkylating the olefins with iso-butane to form high-octane gasoline.

Embodiment 6

A process according to any of the previous embodiments, wherein the first feed stream comprises iso-butane.

Embodiment 7

A process according to any of the previous embodiments, wherein the second feed stream comprises heavy virgin naphtha.

Embodiment 8

A process according to any of the previous embodiments, wherein the second feed stream comprises coker naphtha.

Embodiment 9

A process according to any of the previous embodiments, wherein the second feed stream comprises heavy cat naphtha.

Embodiment 10

A process according to any of the previous embodiments, wherein the second feed stream comprises paraffins in the carbon number range of 7-12.

Embodiment 11

An integrated process for upgrading low-value paraffinic materials to high octane gasoline and high-cetane diesel, comprising, oxidizing iso-butane to form t-butyl hydroperoxide and t-butyl alcohol, catalytically converting the t-butyl hydroperoxide and the t-butyl alcohol to di-t-butyl peroxide, coupling heavy naphtha using di-t-butyl peroxide as a radical initiator to create high-cetane diesel and t-butyl alcohol, converting the t-butyl alcohol to iso-butylene, and alkylating the iso-butylene with iso-butane to form high-octane gasoline.

Embodiment 12

A process according to embodiment 11, wherein the heavy naphtha comprises heavy virgin naphtha.

Embodiment 13

A process according to embodiment 11, wherein the heavy naphtha comprises coker naphtha.

Embodiment 14

A process according to embodiment 11, wherein the heavy naphtha comprises heavy cat naphtha.

Embodiment 15

A process according to embodiment 11, wherein the second feed stream comprises paraffins in the carbon number range of 7-12.

Embodiment 16

An integrated process for upgrading low-value paraffinic materials to high octane gasoline and high-cetane diesel, comprising, oxidizing iso-butane to form t-butyl hydroperoxide and t-butyl alcohol, catalytically converting the t-butyl hydroperoxide and the t-butyl alcohol to di-t-butyl peroxide, coupling heavy naphtha using di-t-butyl peroxide as a radical initiator to create high-cetane diesel and t-butyl alcohol, converting the t-butyl alcohol to iso-butylene, and dimerizing the iso-butylene to form high-octane gasoline.

Embodiment 17

A process according to any of the previous embodiments, wherein the high-cetane diesel has a cetane number greater than 40.

Embodiment 18

A process according to any of the previous embodiments, wherein the high-cetane diesel has a cetane number greater than 45.

Embodiment 19

A process according to any of the previous embodiments, wherein the high-cetane diesel has a cetane number greater than 50.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings therein. It is therefore evident that the particular embodiments disclosed above may be altered or modified and all such variations are considered within the scope and sprit of the present invention. Unless otherwise indicated, all numbers expressing quantities of ingredients, properties, reaction conditions, and so forth, used in the specification and claims are to be understood as approximations based on the desired properties sought to be obtained by the present invention. Whenever a numerical range with a lower limit and an upper limit is disclosed, a number falling within the range is specifically disclosed. Moreover, the indefinite articles "a" or "an", as used in the claims, are defined herein to mean one or more than one of the element that it introduces.

The invention claimed is:

1. An integrated process for upgrading low-value paraffinic materials to high octane gasoline and high-cetane diesel, comprising:
   (a) oxidizing a first feed stream comprising one or more iso-paraffins to form alkyl hydroperoxides and first alcohols;
   (b) catalytically converting the alkyl hydroperoxides and first alcohols to dialkyl peroxides;
   (c) provide a heavy naphtha stream substantially comprising paraffins to couple paraffins with paraffins in heavy naphtha stream using the dialkyl peroxides as a radical initiator to create high-cetane diesel having a cetane number greater than 40 and second alcohols;
   (d) converting the second alcohols to olefins; and
   (e) alkylating the olefins with iso-butane to form high-octane gasoline.

2. The process of claim 1, wherein the first feed stream comprises iso-butane.

3. The process of claim 1, wherein the heavy naphtha stream comprises heavy virgin naphtha.

4. The process of claim 1, wherein the heavy naphtha stream comprises heavy cat naphtha.

5. The process of claim 1, wherein the heavy naphtha stream comprises coker naphtha.

6. The process of claim 1, wherein the heavy naphtha stream comprises paraffins in the carbon number range of 7-12.

7. The process of claim 1, wherein the high-cetane diesel has a cetane number greater than 8.

8. The process of claim 1, wherein the high-cetane diesel has a cetane number greater than 50.

9. An integrated process for upgrading low-value paraffinic materials to high octane gasoline and high-cetane diesel, comprising:
   (a) oxidizing iso-butane to form t-butyl hydroperoxide and t-butyl alcohol;
   (b) catalytically converting the t-butyl hydroperoxide and the t-butyl alcohol to di-t-butyl peroxide;
   (c) provide a heavy naphtha stream substantially comprising paraffins to couple paraffins with paraffins in the heavy naphtha stream using the di-t-butyl peroxide as a radical initiator to create high-cetane diesel having a cetane number greater than 40 and t-butyl alcohol;
   (d) converting the t-butyl alcohol to iso-butylene; and
   (e) dimerizing the iso-butylene to form high-octane gasoline.

10. The process of claim 9, wherein the heavy naphtha comprises heavy virgin naphtha.

11. The process of claim 9, wherein the heavy naphtha comprises heavy cat naphtha.

12. The process of claim 9, wherein the heavy naphtha comprises coker naphtha.

13. The process of claim 9, wherein the high-cetane diesel has a cetane number greater than 45.

14. The process of claim 9, wherein the high-cetane diesel has a cetane number greater than 50.

* * * * *